(12) United States Patent
Katzner et al.

(10) Patent No.: US 7,670,762 B2
(45) Date of Patent: Mar. 2, 2010

(54) BIOCOMPATIBLE TISSUE GRAFT MATERIAL FOR IMPLANT AND METHOD OF MAKING

(75) Inventors: Leo D. Katzner, Shakopee, MN (US); Phillip B. Lawin, New Brighton, MN (US)

(73) Assignee: Brennen Medical, LLC, St. Paul, MN (US)

( * ) Notice: Subject to any disclaimer, the term of this patent is extended or adjusted under 35 U.S.C. 154(b) by 475 days.

(21) Appl. No.: 11/333,597

(22) Filed: Jan. 17, 2006

(65) Prior Publication Data

US 2007/0166397 A1    Jul. 19, 2007

(51) Int. Cl.
*A61K 35/36* (2006.01)

(52) U.S. Cl. .......................... 435/1.2; 435/1.1; 435/1.3; 424/572; 424/543

(58) Field of Classification Search ................. None
See application file for complete search history.

(56) References Cited

U.S. PATENT DOCUMENTS

| | | | |
|---|---|---|---|
| 3,777,599 A | 12/1973 | Reichenbacher et al. | |
| 3,986,926 A | 10/1976 | Monsheimer et al. | |
| 4,175,922 A | 11/1979 | Eckert et al. | |
| 4,300,243 A | 11/1981 | Baumgartner | |
| 4,424,208 A | 1/1984 | Wallace et al. | |
| 4,581,148 A | 4/1986 | Swanson et al. | |
| 4,776,853 A | 10/1988 | Klement et al. | |
| 4,801,299 A | 1/1989 | Brendel et al. | |
| 4,911,710 A | 3/1990 | Milthorpe et al. | |
| 4,960,428 A | 10/1990 | Christner et al. | |
| 5,078,744 A * | 1/1992 | Chvapil | 606/86 R |
| 5,104,405 A | 4/1992 | Nimni | |
| 5,108,424 A | 4/1992 | Hoffman, Jr. et al. | |
| 5,141,747 A | 8/1992 | Scholz | |
| 5,263,983 A | 11/1993 | Yoshizato et al. | |
| 5,332,475 A | 7/1994 | Mechanic | |
| 5,376,042 A | 12/1994 | Reber et al. | |
| 5,387,278 A | 2/1995 | Mangialardi | |
| 5,397,353 A | 3/1995 | Oliver et al. | |
| 5,447,536 A | 9/1995 | Girardot et al. | |
| 5,571,216 A | 11/1996 | Anderson | |
| 5,855,620 A | 1/1999 | Bishopric et al. | |
| 5,916,265 A | 6/1999 | Hu | |
| 5,931,969 A | 8/1999 | Carpentier et al. | |
| 6,220,951 B1 | 4/2001 | Clayton et al. | |
| 6,391,939 B2 | 5/2002 | Tayot et al. | |
| 6,458,889 B1 | 10/2002 | Trollsas et al. | |
| 6,482,240 B1 | 11/2002 | Eckmayer et al. | |
| 6,652,594 B2 | 11/2003 | Francis et al. | |
| 6,670,454 B2 | 12/2003 | Lai et al. | |
| 6,706,684 B1 | 3/2004 | Bayon et al. | |
| 6,910,354 B2 | 6/2005 | Ciucani | |
| 6,933,103 B1 | 8/2005 | Klein et al. | |
| 2003/0003153 A1 | 1/2003 | Asculai et al. | |
| 2004/0059356 A1 | 3/2004 | Gingras | |
| 2004/0078076 A1 | 4/2004 | Badylak et al. | |

OTHER PUBLICATIONS

Tutoplast® product brochure, Biodynamics International, Inc., 8 pgs.

* cited by examiner

*Primary Examiner*—Allison M Ford
(74) *Attorney, Agent, or Firm*—Faegre & Benson LLP

(57) ABSTRACT

This invention provides an antigen-free and immunologically inert tissue graft material and methods of preparing and using these tissue graft materials.

9 Claims, No Drawings

BIOCOMPATIBLE TISSUE GRAFT MATERIAL FOR IMPLANT AND METHOD OF MAKING

BACKGROUND

In treating many illnesses and injuries, it is often useful to replace or reinforce damaged or injured tissues with a biocompatible graft material. Examples of such graft materials are diverse and include, but are not limited to: coronary grafts, such as arteries, veins, and valves; structural tissues, such as ligaments and tendons, dura mater, and skin. The suitable graft materials may also be used for surgical procedures such as slings for the treatment of urinary incontinence, bulking agents for cosmetic or reconstructive surgery, heart valve replacements, pericardium repairs, arterial transplants, and surgical meshes for the repair of hernias, abdominal wall reconstructions, and pelvic floor reconstructions. Suitable graft materials may be derived from allogenic or exogenic sources. Furthermore, allogenic graft materials may further be derived from autologous or homologous sources and may even include cadaveric sources.

The use of biocompatible grafts is an important and sometimes indispensable part of a course of treatment. However, to avoid, dangerously adverse reactions in a patient being treated with a biocompatible graft, it is first necessary to treat a freshly harvested graft material before it may be used as intended. This is particularly true where graft materials are derived from exogenic and homologous sources. Typically autologous sources of graft material represent a much lower risk with regard to adverse reactions but treatment may still be desired for the graft material to further reduce the likelihood of adverse reactions.

Freshly harvested graft materials are treated to remove any type of reactive material that may be present in the graft material, such as antigens, viruses and prions. Once such reactive material is removed, the graft may be emplaced. Removal of reactive cellular materials leaves behind an immunologically inert structural component of the graft alone. The structural component of a graft is an extra cellular matrix comprised of collagen fibers that are by themselves typically biochemically inert. The failure to remove reactive cellular material from the extra cellular matrix can cause severe reactions to the graft material that can extend healing time or even result in the complete rejection of the graft material itself.

Much work has been done in the field of decellularizing human and animal tissue to yield an essentially inert extra cellular matrix useful as a graft material. Typically, other technologies essentially use crosslinking or alkylation to mask the antigens or enzymes or caustic solutions to remove the antigens. While these methods may produce useful biocompatible graft materials, these methods have limitations in terms of their complexity, their expense, their ability to remove (rather than mask) antigens, their ability to remove hair, or controlling the rate of absorption.

SUMMARY

One embodiment of the present invention provides an endotoxin-free, antigen-free and immunologically inert implantable graft material that is configured to a shape and thickness to delay bioabsorption or remodeling and to increase resistance to enzymatic degradation. Other embodiments of the present invention provide for an implant material that is substantially hair-free and immunologically inert. Methods for preparing such a graft material are also provided.

The method of preparing the graft collagenic material includes reducing or removing proteins and non-collagenic tissue, such as antigens, with a mixture of a caustic and peroxide solution and preparing the graft material for storage and/or use. In one embodiment, the mixture of caustic and peroxide solution may include a 1N (1 Normal) sodium hydroxide solution and a 3 w % solution of hydrogen peroxide. An optional step of chemically cross-linking the graft material is also provided.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the detailed description is to be regarded as illustrative in nature and not restrictive.

DETAILED DESCRIPTION

The present invention generally provides an implantable graft material that is endotoxin-free, antigen-free, and immunologically inert and is configured to a shape and thickness to delay bioabsorption or remodeling and to increase resistance to enzymatic degradation. Also methods for producing such a graft material are provided for. As used in this specification, "antigen-free" refers to tissue material in which antigens are entirely or substantially removed from the tissues. Other embodiments of the invention provide for an implantable graft material that is absorbable remodelable, collegenic graft material that is "substantially hair-free" and immunologically inert. As used in this specification, "remodelable" refers to a material that can be broken down and resorbed without giving rise to adverse reactions and that is capable of conforming to the body by promoting and controlling the re-vascularization, re-population and regeneration of new tissue. As used in this specification, "substantially hair-free" refers to graft material obtained by the method of the present invention. Unless otherwise specified, all stated percentages are given by weight (wt %).

The source of the animal tissue may be derived from an autologous, heterologous or allogenic source. The graft material may be made from tissue obtained from human or animals. Animals include pigs, sheep, cows, goats, horses or other such animals. The animal tissues used may include skin, artery, heart valve, bone pericardium, fascia or dura mater.

One embodiment of the present invention provides a method for producing collegenic graft material. The method includes the steps of isolating and treating the derma layers of porcine tissue and lysing non-collagenic cell material by using "osmotic pressure gradients." As used in this specification, the term "osmotic pressure gradients" refer to soaking tissues alternately in increasingly hypertonic and hypotonic solutions. The methods further include altering proteins and non-collagenic tissue by treating the graft material with a mixture of sodium hydroxide and hydrogen peroxide, and preparing the graft material for storage and/or use. Although the following description is directed toward porcine tissue or skin, embodiments of the present invention may be suitable for other types of graft material.

In certain embodiments, suitable porcine tissues are procured and after an initial washing, are soaked in sodium hypochlorite bleach solution for the purpose of destroying bacteria and viruses. The tissue may be soaked, for example, for 30-45 minutes. The tissues are then frozen. While this freezing step does help to burst cells within the extra cellular matrix, it is essentially one of convenience and can be omitted if so desired. It is, however, necessary to soak the porcine tissues in a bleach or equivalent solution to reduce the level of microbial agents present in the hides. Suitable alternatives to sodium hypochlorite that may be used in the first procurement step and in the freezing and thawing steps include hydrogen peroxide, calcium hypochlorite and iodophor solutions such as povidone-iodine.

The frozen porcine tissues are next placed in sodium hypochlorite bleach solution and thawed therein for approximately 12 to 16 hours. In certain embodiments, the tissues are placed in a 0.1 to 0.2% sodium hypochlorite solution.

The tissues are then configured to a desired size, shape and thickness. In one embodiment, the rinsed tissues are cut into strips of a suitable size.

The strips of porcine tissue are next placed in a detergent solution to remove fats and greases therefrom. This detergent solution may also remove the cellular membrane and proteins by disrupting lipids. Bleach may also be added to the detergent solution for the purposes of destroying bacteria and viruses. In one embodiment, the porcine tissue is preferably soaked in the aforementioned detergent solution for approximately one half hour. During soaking in the detergent solution, the porcine tissue may be shaved to remove exterior hair shafts.

The porcine tissue is next rinsed in purified or tap water for approximately two hours. During this rinsing step, the epidermis and dermis are removed from the tissue using a dermatome to obtain a suitable thickness. The thickness may vary depending upon the desired final thickness of the graft material. For example, tissue material may be prepared with thickness ranging between about 0.02 to about 0.1 inches. In one embodiment, the tissue material has a thickness of 0.035 to 0.048 inches. In another embodiment, the tissue material has a thickness between 0.07 to 0.1 inches.

Varying the thickness affects the rate of absorption within the body when the material is acted upon by degradation or enzymes such as collagenase.

Collagenases are a class of enzymes that break down the native collagen that holds animal tissues together and are made by a variety of microorganisms and by many different animal cells. Collagenase is one of the body's natural mechanisms for absorbing and remodeling collagen. Hence, collagenase can be used to determine the rate of break down or absorption of a material by a mammalian host.

The porcine tissue is next transferred to a first iodophor solution. In one embodiment, a 7.5% povidone-iodine was used and the porcine tissue allowed to soak for approximately 2 hours. In other embodiments, the porcine tissue, as strips were removed temporarily from the iodophor scrub solution so that additional hair stubble may be removed by shaving. When the porcine tissue strips have been soaked for a sufficient amount of time in the first iodophor scrub solution the tissue is then rinsed in water and transferred to another iodophor solution, for example, 10% povidone-iodine, for approximately one half hour to further reduce the bioburden level of non-collagenic cellular materials present in the porcine tissue samples. After this second iodophor solution soak, the porcine tissue strips are again rinsed in water, this time for approximately 3 hours. After rinsing, the porcine tissues are trimmed to their final dimensions.

In an alternate embodiment, the porcine tissue may be treated with a bleach solution containing sodium hypochlorite or calcium hypochlorite.

The portions of porcine tissue are next measured and sorted into batches of known surface area. Each batch of porcine tissue may optionally be treated with an antibiotic solution to remove unwanted bacteria. In one embodiment, the porcine tissue is treated with a concentration of an antibiotic solution of approximately 2000 milliliters for every 5 square feet of porcine tissue. Antibiotics that may be used include 0.05% kanamycin sulfate in a 0.9% saline solution. Other suitable antibiotics include neomycin, bacitracin, tetracycline and other antibiotics.

After treatment with antibiotics, the respective batches of porcine tissue are then soaked alternately in increasingly hypertonic and hypotonic solutions for 2-hour intervals. In one embodiment, the hypertonic solutions include 2%, 4%, 6%, 8%, 10% and 12% sodium chloride in purified water. The hypotonic solution may include purified water. Each treatment consists of a 2-hour soak with or without agitation. Therefore, this step in the production of an immunologically inert graft material requires 12 two-hour treatments for a total of approximately 24 hours. For example, a batch of porcine tissue is placed in the hypertonic 2% saline solution for two hours. Thereafter this batch of porcine tissue is placed in the hypotonic purified water for two hours and then into a hypertonic 4% saline solution for two hours. This process continues through the 12% saline solution.

The treatment of the porcine tissue batch with alternating hypertonic and hypotonic solutions acts to rupture cellular membranes by creating an osmotic pressure gradient across the cellular membranes. The cyclic nature of raising and lowering osmotic pressures using hypertonic and hypotonic solutions has been found very effective in lysing the cells present in the tissue. Gradually increasing the concentration of the hypertonic solutions is a preferred means of increasing this lysing action.

In some embodiments, the concentration of the hypertonic solutions may include 1%, 3%, 5%, 7%, 9%, and 11% solutions and other series of increasingly concentrated solutions. Any ionic aqueous solution that is compatible with the intended use of the porcine tissue will be suitable for use as a hypertonic solution in this treatment. Similarly, any non-ionic aqueous solution that is compatible with the intended use of the porcine tissue will be suitable for use as a hypotonic solution in this treatment.

Following the last hypotonic solution rinse, the porcine tissue is then placed in a mixture of a caustic and peroxide solution. In one embodiment, a 1N sodium hydroxide solution and a 3% solution of hydrogen peroxide is used for approximately two hours. In some embodiments the ranges of sodium hydroxide that may be used are from 0.1N to 5N, and ranges for hydrogen peroxide include between about 0.1 and 20%. In other embodiments the ranges of sodium hydroxide that may be used are from 0.25-3N, and ranges for hydrogen peroxide include between about 0.75%-10%. In still other embodiments, the peroxide solution concentration used is between 1-3%. Alternate embodiments of this step may involve treating the porcine tissue with functional equivalents of sodium hydroxide, for example, potassium hydroxide, ammonium hydroxide, calcium hydroxide, sodium dodecylsulfate, urea, phenol, or formic acid. Alternative or functional equivalents of hydrogen peroxide, for example, include peracetic acid, perbenzoic acid, benzoyl peroxide, sodium peroxide, or potassium permanganate.

The treatment of the porcine tissue with the mixture of a caustic and peroxide solution removes the epidermis from the tissue and the majority of any remaining hair stubble that may be contained or trapped in the pores of the porcine tissue as well as destroys the non-collagenus material, for example, antigens. The porcine tissue is also bleached. This step may be performed under agitation in a reaction chamber as disclosed in U.S. Pat. No. 6,933,103, which is incorporated herein by reference.

The porcine tissue is agitated during this soaking step with a paddle mixer of known type running at approximately 120 rotations per minute. After the porcine tissue has been treated for its allotted time in the sodium hydroxide and hydrogen peroxide solution, the porcine tissue is then placed in water and agitated using a paddle mixer running at approximately 120 rotations per minute. This water rinse is essentially a polishing step that is a continuation of the sodium hydroxide and hydrogen peroxide treatment of the previous step due to the carryover of hydroxide ions from that previous step. Typically the pH of the purified water rinse will rise and become highly caustic but less caustic than the first sodium hydroxide solution. This slightly lower pH is less destructive to the collagen of the porcine tissue's extra cellular matrix, but will continue to remove non-collagenic cellular material from the extra cellular matrix.

Upon removal from the reaction chamber, the porcine tissue is rinsed in water for approximately one hour. This rinsing step may be carried out multiple times. This rinsing step removes pyrogens and hydrogen peroxide and hydroxyl ion carryover from the extracellular matrix of the porcine tissue. At this stage the porcine tissue has had substantially all of the non-collagenic cellular material, such as antigens, removed from the extra cellular matrix thereof.

In an optional step, after the water rinses, the resulting immunological inert porcine tissue may be chemically cross-linked with a cross-linking agent.

Aldehydes and other cross-linking agents have been used in tissue implants to cross-link and bind antigens as a means of reducing antigenicity. Oftentimes the undesirable side-effect of binding antigens is cross-linking the tissue to such a degree that adversely delays or prevents absorption by the body. Furthermore, when a cross-linking agent is used to mask or sequester antigens, any spontaneous breakage of the sequestration bond releases the antigen and causes localized antigenic responses which may cause implant failure. In the present invention, the cross-linking agent is not necessary for reducing antigenicity because the tissue is already antigen-free. Therefore, the cross-linking agent can be used solely for the purpose of controlling the rate of absorption by the body.

Depending upon the degree of cross-linking desired, the cross-linking treatment used is in the range between about 0.01 to 5%. In one embodiment gluteraldehyde is used at a 1.5% concentration. Other suitable cross-linking agents that may be used include aldehyde, formaldehyde, dialdehydes, dialdehyde starch, carodiamides, epoxies and isoycanates.

The cross-linked tissue is then rinsed in water and further subjected to an optional solution of hydrogen peroxide for an additional one hour. This step bleaches the tissue to a nearly white color.

In some embodiments, after the final water rinses, in either the cross-linked or non-cross-linked tissue, the tissue is soaked in a 0.9% saline solution for approximately half an hour to stabilize the porcine tissue and make it isotonic with respect to a recipient of the graft.

The porcine tissue is now an antigen-free and immunologically inert graft material that is ready for implantation. The porcine graft material may then be packaged, labeled and sterilized and conserved for future use. One alternative to standard packaging and sterilization is to freeze dry the porcine graft material.

As indicated above, a graft material produced according to the method of the present invention includes a collagenic extra cellular matrix from which substantially all of the bioreactive cellular material has been removed. The graft materials produced by the method of the present invention may be used for surgical procedures such as slings for treatment for urinary incontinence, surgical meshes for repair of hernias, bulking agents for cosmetic or reconstructive surgery, abdominal wall reconstructions, pelvic floor reconstructions, heart valve replacements, pericardium repairs, or arterial transplants.

Preparation of Tissue Material

Three versions of mesh were made, by the methods described herein, for testing differing rates of absorption. The first version was made using porcine skin cut at a thickness of 0.035 inches to 0.048 inches. The second version was made using porcine skin cut at a thickness of 0.070 inches to 0.100 inches. The third version was made using porcine skin cut at a thickness of 0.035 inches to 0.048 and subsequently treated with glutaraldehyde at a concentration of 1.5%.

Treatment with collagenase was used to simulate absorption by the body of a collagen implant. The collagenase used was a type 1A obtained from Sigma Aldrich, catalogue number C-2674. After sterilization, each of the versions were placed in a 20 mg/mL collagenase solution at the rate of 0.89 mL collagenase solution per square centimeter of tissue. The different versions of tissues were incubated at 35° C. for 48 hours.

Measure of Pull and Tensile Strength

A snapshot in time of the strength of a porcine dermis after reaction with a known amount of collagenase at constant temperature is determined by measuring pull and tensile strength. Pull and tensile strength is used as a measure of collagen integrity, thus absorption. The relative strength of porcine dermis at any given time is equivalent to relative time required to retain any given strength. In this manner, one can use the presented data as a representation of the relative absorption rates of treated porcine dermis by the body.

To measure the pull strength of the tissue samples, the samples were cut in the shape of an hourglass. The dimensions of the neck or narrow region of the hourglass-shaped tissue samples were approximately 0.5 inches by 0.5 inches. The thicknesses of the samples were also measured in this region. The samples were placed in an Instron® or similar measurement device and stretched to the point of failure. The maximum force (in pounds) required to tear apart the tissue was recorded. The force (in pounds) divided by the width (in inches) results in the pull strength in pounds/linear inch.

The measure of tensile strength was determined by dividing the force by the thickness (in inches) resulting in the tensile strength in pounds/square inch.

EXAMPLE 1

The following table shows the results of subjecting different versions of treated porcine dermis with collagenase.

| Test No. | Version | Collagenase | Pull Strength Lbs/in | Tensile Strength Lbs/in$^2$ |
|---|---|---|---|---|
| 1 | Thin | collagenase @ 20 mg/mL | 2.76 | 71.6 |
| 2 | Thick | collagenase @ 20 mg/mL | 46.68 | 258.5 |
| 3 | Thin with Glutaraldehyde | collagenase @ 20 mg/mL | 51.76 | 956.8 |
| 4 | Thin - Control | none | 84.34 | 1500.0 |

This table shows the porcine tissue control (material made according to this patent) is initially very strong—84.34 lbs/in pull strength (Test 4). When implanted the porcine implant will be absorbed and remodeled by the body. In the presence of collagenase the thin porcine implant is broken down, absorbed, as evident by the reduced pull and tensile strengths—2.76 and 71.6 lbs/in respectively (Test 1). By increasing the thickness the implant retained substantial strength as seen by Test 2—46.68 lbs/in compared with 2.76 for the thin version. By treating the thin version with glutaraldehyde the rate of break down or absorption is further reduced as is evident by Test 3—51.76 lbs/in. In this manner, the desired absorption can be adjusted by changing the thickness and/or cross-linking of the implant.

The invention is claimed:

1. A method of preparing an absorbable remodelable graft material that is substantially hair-free and immunologically inert comprising the steps of:
   (a) soaking an animal tissue in a bleach solution;
   (b) washing the animal tissue in a detergent solution;
   (c) rinsing the animal tissue to remove the detergent solution;
   (d) configuring the animal tissue to a desired physical form and thickness;
   (e) soaking the animal tissue in an iodophor solution;
   (f) rinsing the animal tissue to remove the iodophor solution;
   (g) soaking the animal tissue in a hypertonic solution;
   (h) rinsing the animal tissue to remove the hypertonic solution;
   (i) agitating the animal tissue in a mixture of a caustic and peroxide solution; and
   (j) rinsing the animal tissue in water to remove the mixture of caustic and peroxide solution to provide the absorbable remodelable graft material that is a collagenic extra cellular matrix from which substantially all bioreactive cellular material is removed and is substantially hair-free.

2. The method of claim 1, wherein the step of soaking the animal tissue in a hypertonic solution further comprises the steps of:
   soaking the animal tissue in a series of increasingly hypertonic solutions; and
   rinsing the animal tissue after each soaking in a hypotonic solution to remove the hypertonic solution.

3. The method of claim 1, wherein the mixture of a caustic and peroxide solution comprises a sodium hydroxide concentration between about 0.1-5N and a peroxide concentration between about 0.1-20 wt %.

4. The method of claim 1, wherein the mixture of a caustic and peroxide solution comprises a sodium hydroxide concentration between about 0.25-3N and a peroxide concentration between about 0.75-10 wt %.

5. The method of claim 1, wherein the graft material is soaked in a saline solution after step (j).

6. The method of claim 1, wherein the graft material is chemically cross-linked to modify its absorption rate, after step (j).

7. The method of claim 6, wherein the graft material is chemically cross-linked with a cross-linking agent at a concentration of about 0.01 to about 5 percent.

8. The method of claim 1 wherein the animal tissue is from an autologous, heterologous or allogenic source and derived from porcine, bovine, equine, rodent or human tissue.

9. The method of claim 1, wherein the animal tissue comprises porcine derma tissue.

* * * * *